(12) United States Patent
Temple et al.

(10) Patent No.: US 11,160,208 B2
(45) Date of Patent: Nov. 2, 2021

(54) METHOD AND APPARATUS FOR SENSING CROP MATERIAL IN A HARVESTER

(71) Applicant: Deere & Company, Moline, IL (US)

(72) Inventors: Douglas G. Temple, Fulton, IL (US); Alexander B. Lassers, Davenport, IA (US); Nithin Choudary, Bettendorf, IA (US)

(73) Assignee: DEERE & COMPANY, Moline, IL (US)

( * ) Notice: Subject to any disclaimer, the term of this patent is extended or adjusted under 35 U.S.C. 154(b) by 294 days.

(21) Appl. No.: 16/397,462

(22) Filed: Apr. 29, 2019

(65) Prior Publication Data

US 2020/0337234 A1 Oct. 29, 2020

(51) Int. Cl.
| | |
|---|---|
| *A01D 41/127* | (2006.01) |
| *A01D 41/14* | (2006.01) |
| *A01F 12/46* | (2006.01) |
| *G01N 21/3554* | (2014.01) |
| *G01N 25/56* | (2006.01) |
| *A01D 89/00* | (2006.01) |
| *G01N 21/85* | (2006.01) |
| *G01N 19/10* | (2006.01) |

(Continued)

(52) U.S. Cl.
CPC .......... *A01D 41/127* (2013.01); *A01D 41/14* (2013.01); *A01F 12/46* (2013.01); *G01N 21/3554* (2013.01); *G01N 25/56* (2013.01); *A01D 89/008* (2013.01); *G01N 19/10* (2013.01); *G01N 21/3563* (2013.01); *G01N 21/85* (2013.01); *G01N 27/223* (2013.01); *G01N 2021/157* (2013.01); *G01N 2021/3155* (2013.01); *G01N 2021/8592* (2013.01); *G01N 2033/245* (2013.01)

(58) Field of Classification Search
CPC ..... G01N 2033/245; G01N 2021/8592; G01N 2021/3155; G01N 2021/157; G01N 27/223; G01N 25/56; G01N 21/85; G01N 21/3563; G01N 21/3554; G01N 19/10; A01F 12/46; A01D 61/008; A01D 41/14; A01D 41/1277; A01D 41/127
See application file for complete search history.

(56) References Cited

U.S. PATENT DOCUMENTS 4,403,191 A * 9/1983 Satake ................... G01N 33/10
324/452
5,092,819 A 3/1992 Schroeder et al.
(Continued)

FOREIGN PATENT DOCUMENTS

EP 0958728 A1 11/1999

*Primary Examiner* — Arpad Fabian-Kovacs
(74) *Attorney, Agent, or Firm* — Michael Best & Friedrich LLP (57) ABSTRACT

A sensing system and method is provided for crop material in a harvester. The sensing system includes a conveyor auger device oriented in a substantially vertical direction and having an entrance aperture, an exit aperture located upwardly above a radially oriented sensing aperture disposed therebetween. The conveyor auger device includes a conveyor auger having a flight for moving crop material upwardly, wherein the flight has a reduced radial extension adjacent the sensing aperture. A sensor disposed at or adjacent the sensing aperture senses the essentially continuously upwardly moving crop material for determining a property thereof.

19 Claims, 6 Drawing Sheets

(51) Int. Cl.
  *G01N 21/15* (2006.01)
  *G01N 21/3563* (2014.01)
  *G01N 21/31* (2006.01)
  *G01N 33/24* (2006.01)
  *G01N 27/22* (2006.01)

(56) References Cited

U.S. PATENT DOCUMENTS

| | | | | |
|---|---|---|---|---|
| 5,106,339 A | * | 4/1992 | Braun | A01D 41/1277 460/7 |
| 6,083,103 A | | 7/2000 | Posselius et al. | |
| 6,100,526 A | * | 8/2000 | Mayes | G01N 21/359 250/339.11 |
| 6,125,620 A | * | 10/2000 | Posselius | A01D 41/1277 460/7 |
| 6,155,103 A | | 12/2000 | Diekhans et al. | |
| 6,389,884 B1 | * | 5/2002 | Diekhans | A01D 41/127 460/7 |
| 6,421,990 B1 | * | 7/2002 | Ohlemeyer | A01D 41/127 356/328 |
| 6,460,008 B1 | * | 10/2002 | Hardt | A01D 41/1272 460/1 |
| 6,471,032 B2 | * | 10/2002 | Busschaert | A01D 41/1271 198/300 |
| 7,771,262 B2 | * | 8/2010 | Missotten | G01N 21/85 460/114 |
| 8,045,168 B2 | * | 10/2011 | Missotten | G01N 21/94 356/445 |
| 8,218,912 B2 | * | 7/2012 | Missotten | A01D 41/1277 382/309 |
| 8,961,283 B2 | * | 2/2015 | Claussen | G01N 21/85 460/1 |
| 9,506,786 B2 | * | 11/2016 | Strnad | G01F 1/20 |
| 10,159,191 B2 | * | 12/2018 | Andrios | A01D 41/1274 |
| 10,188,036 B2 | * | 1/2019 | Loukili | A01D 41/127 |
| 2005/0195406 A1 | * | 9/2005 | Kormann | A01D 43/085 356/500 |
| 2011/0086684 A1 | * | 4/2011 | Luellen | A01D 41/1277 460/79 |
| 2014/0365170 A1 | * | 12/2014 | Van Mill | A01D 90/12 702/173 |
| 2017/0049050 A1 | * | 2/2017 | Lenaerts | A01F 12/60 |
| 2017/0112056 A1 | * | 4/2017 | Sierra | A01D 41/127 |
| 2017/0118914 A1 | * | 5/2017 | Bruns | A01D 41/1272 |
| 2018/0087939 A1 | * | 3/2018 | Brandmeier | A01D 41/1271 |
| 2018/0153100 A1 | * | 6/2018 | Takahara | G01N 21/85 |

* cited by examiner

METHOD AND APPARATUS FOR SENSING CROP MATERIAL IN A HARVESTER

BACKGROUND

The present disclosure relates to a method and an apparatus provided in a harvesting machine for moving crop material along an upwardly oriented path to pass a sensor that determines constituents or properties thereof.

SUMMARY

In one embodiment, the disclosure provides a sensing system for sensing a property of a crop material harvested by a harvester. The system includes a conveyor auger device oriented in a substantially vertical direction. The conveyor auger device includes a radially oriented sensing aperture, and a radially oriented exit aperture disposed upwardly above the sensing aperture. A conveyor auger disposed in the conveyor auger device includes a flight for moving the crop material upwardly, wherein the flight has a reduced in radial extension adjacent the sensing aperture. The system includes a sensor disposed at or adjacent the sensing aperture for sensing the crop material that is moving essentially continuously upwardly for determining a property thereof.

In another embodiment, a crop material transfer arrangement includes a sensing system for sensing a property of a crop material harvested by a harvester. The sensing system includes a transfer auger configured to advance crop material; an elevator configured to receive crop material from the transfer auger, the elevator including a drive arrangement for moving the crop material to a storage tank of the harvester; and a conveyor auger device oriented in a substantially vertical direction and configured to receive crop material from a bottom of the elevator and configured to return crop material to the elevator. The conveyor auger device includes a radially oriented sensing aperture, a radially oriented exit aperture disposed upwardly above the sensing aperture, and a conveyor auger including a flight for moving the crop material upwardly, wherein the flight has a reduced radial extension adjacent the sensing aperture. The sensing system includes a sensor disposed at or adjacent the sensing aperture for sensing the crop material that is moving essentially continuously upwardly for determining a property thereof.

In another embodiment, the disclosure provides a method for sensing a property of a crop material harvested by a harvester. The method includes operating a conveyor auger to move the crop material generally upwardly within a conveyor auger device, the conveyor auger device having a sensing aperture and providing a sensor at or in the sensing aperture of the conveyor auger device. The method further includes sensing essentially continuously upwardly moving crop material with the sensor disposed at the sensing aperture and from the sensed information, determining a property of the crop material.

Other aspects of the disclosure will become apparent by consideration of the detailed description and accompanying drawings.

DETAILED DESCRIPTION

Before any embodiments of the disclosure are explained in detail, it is to be understood that the disclosure is not limited in its application to the details of construction and the arrangement of components set forth in the following description or illustrated in the following drawings. The disclosure is capable of supporting other embodiments and of being practiced or of being carried out in various ways.

Figure 1:
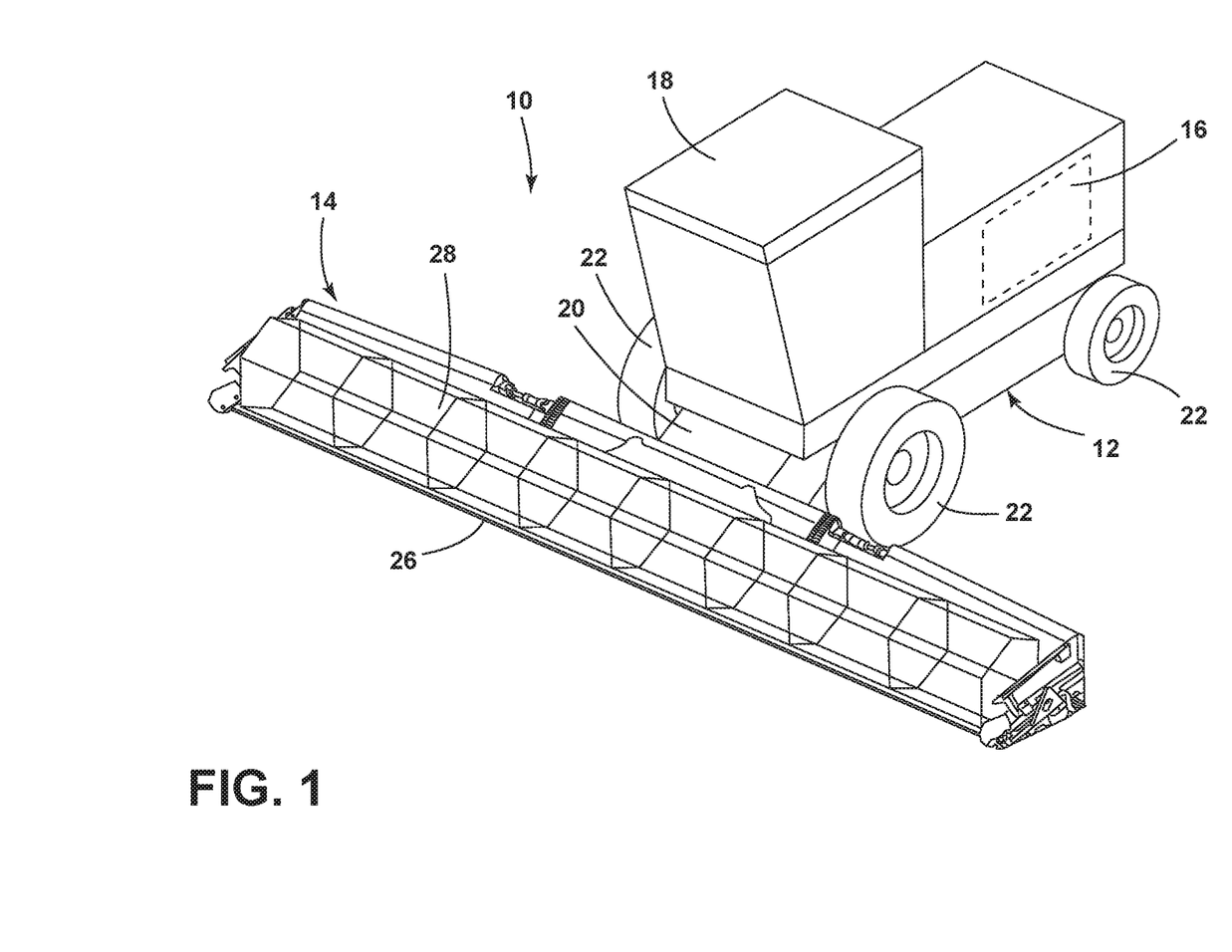
FIG. 1 is a perspective view of a harvester.

FIG. 1 illustrates a harvester 10 according to some embodiments. The illustrated harvester 10 includes a combine 12 and a harvesting platform 14. The combine 12 includes a prime mover 16, a cab 18, a feeder house 20, and a plurality of ground-engaging devices 22. The prime mover 16 is configured to move the combine 12 in a direction of travel via the ground-engaging devices 22. The illustrated ground-engaging devices 22 are wheels, but tracks or other suitable ground-engaging devices can be utilized.

In one embodiment, the harvesting platform 14 includes a cutter bar 26 configured to cut grain being harvested, and a reel 28 configured to press the grain against the cutter bar to thereby cut the grain.

Figure 2:
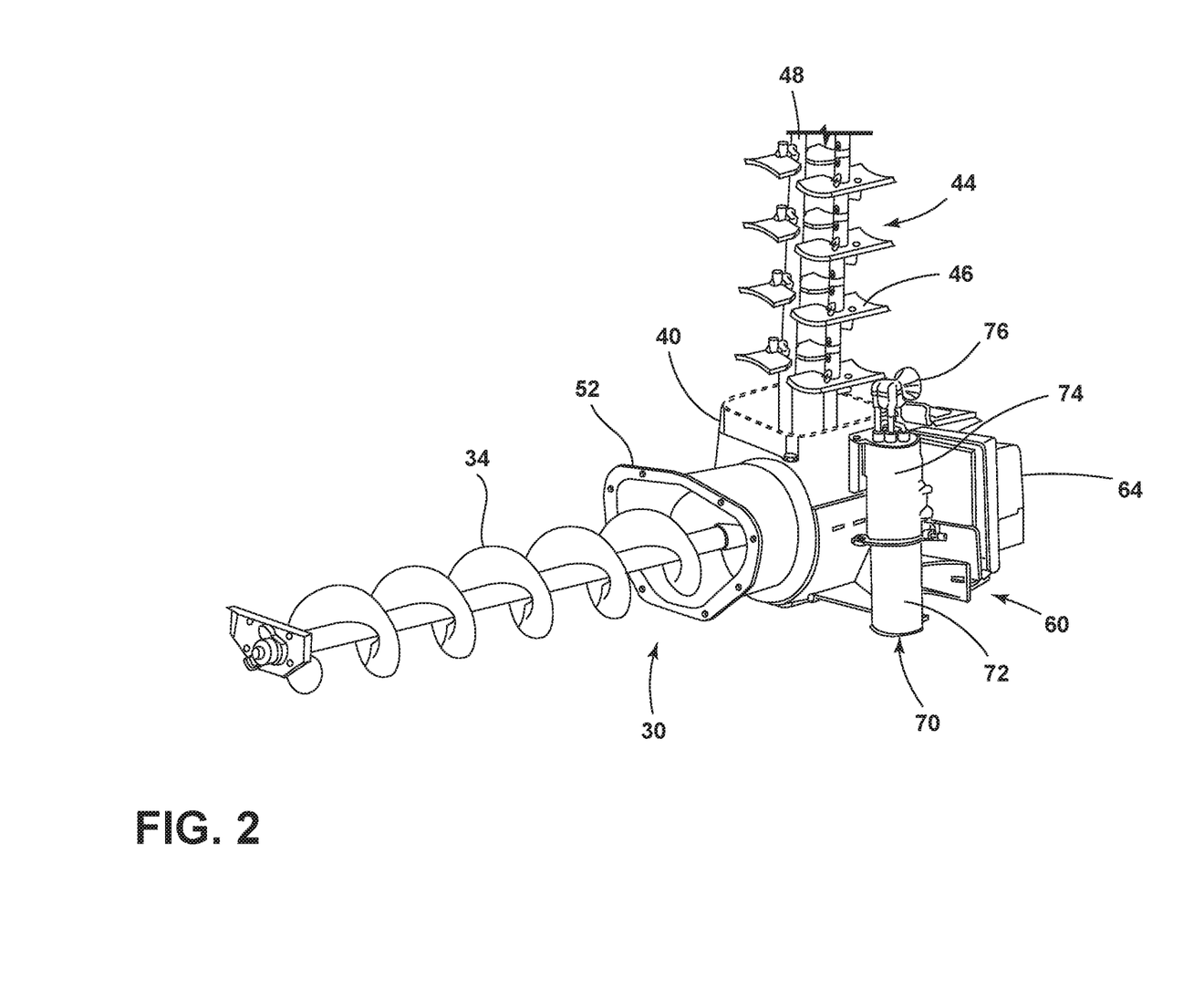
FIG. 2 is a perspective partial view of a crop material transfer arrangement for a harvester with a cut-away of a portion of the elevator to show a chain and paddle conveyor.

FIG. 2 illustrates a perspective partial view of one embodiment of a crop material transfer arrangement 30 that includes a transfer auger 34 for providing crop material to an elevator 40. A top portion of the elevator is removed to show a chain and paddle conveyor 44 provided therein than includes paddles 46 and a chain 48 to move crop material upwardly to an upper storage compartment of the harvester 10. Other drive arrangements besides the chain and paddle conveyor 44 are contemplated. FIG. 2 also shows an elevator receiver 52 for receiving crop material carried or driven by the transfer auger 34.

A sensing system 60 includes a sensor 64 and a conveyor auger device 70 that supports the sensor. The conveyor auger device 70 includes a conveyor housing defined by a lower conveyor housing portion 72 and an upper conveyor housing portion 74 as shown in FIG. 2. A conveyor auger drive 76 secured at a top thereof in FIG. 2 provides power to rotate a conveyor auger 80 shown in FIG. 3 that is contained therein. The conveyor auger device 70 is oriented in a substantially vertical or upward direction.

Figure 3:
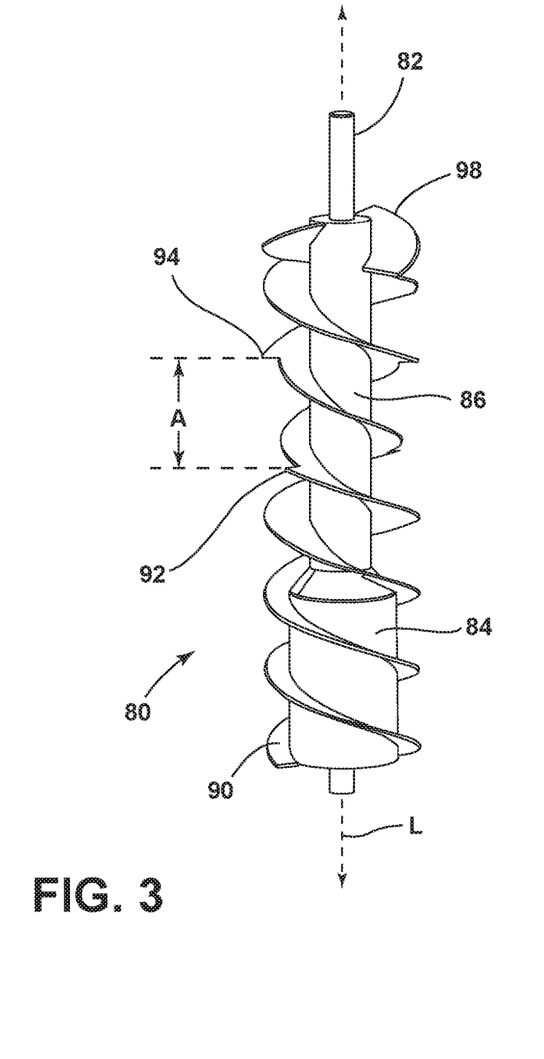
FIG. 3 is a perspective view of a conveyor auger.
Figure 4:
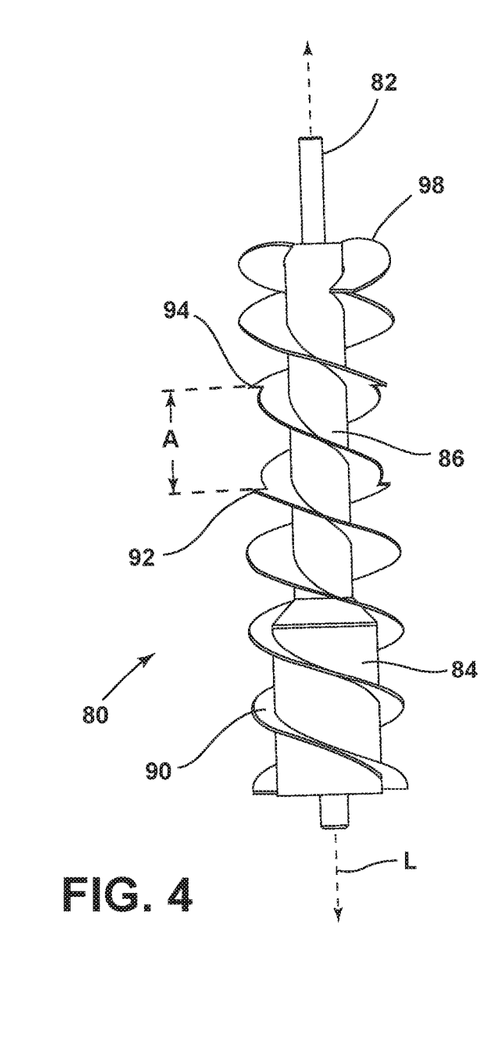
FIG. 4 is another perspective view of the conveyor auger shown in FIG. 3.

The conveyor auger 80 shown in FIG. 3 includes driven shaft 82 for rotating the auger about a longitudinal axis L defined thereby. Further, the conveyor auger 80 includes a drum 84 at a base thereof that has a greater diameter than an upper cylindrical member 86 of the conveyor auger. A flight 90 extends continuously about the drum 84 and then about the upper cylindrical member 86. The flight 90, however, has a reduced radial extension or width projecting orthogonally relative to the longitudinal axis L in a generally upper middle section A thereof defined between projections 92, 94. Upwardly, from the projection 94, the flight 90 again has an increased radial extension projecting orthogonal with respect to the longitudinal axis L that is essentially the same as the radial extension of the flight 90 below the projection 92 shown in FIG. 3. Thus, section A as defined by horizontal dashed lines, indicates a region or longitudinal linear distance where the flight dimension is reduced. At an upper end thereof, the conveyor auger 80 has a reverse flight 98 for the purpose of ejecting crop material radially outwardly from the conveyor auger device 70. FIG. 4 represents the same conveyor auger 80 as in FIG. 3 provided at a different perspective view to further illustrate the features thereof.

Figure 5:
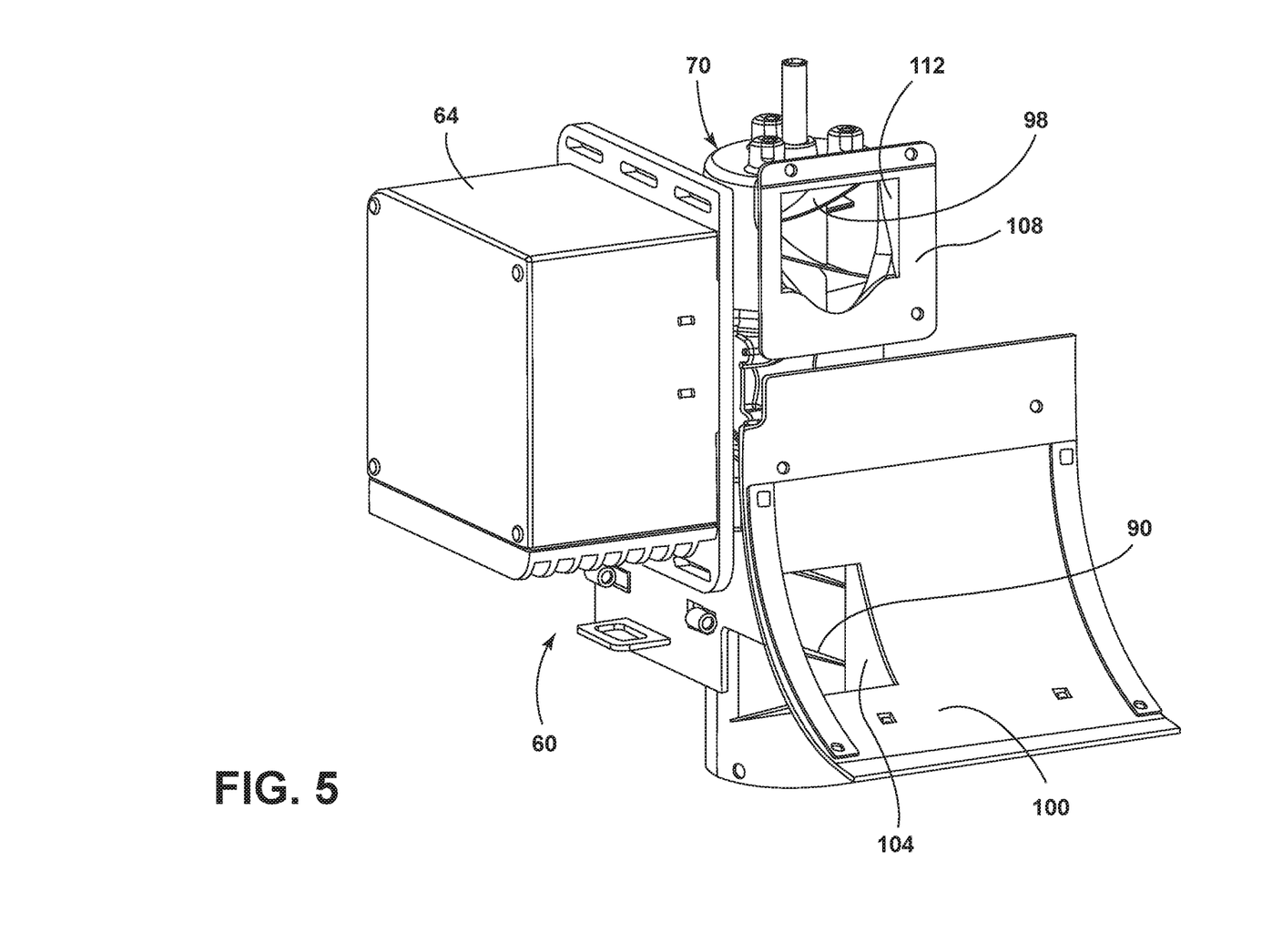
FIG. 5 is a perspective view of a sensing system including a sensor and a conveyor auger device.

FIG. 5 shows one embodiment of the sensing system 60 including the sensor 64 and the conveyor auger device 70. The conveyor auger device 70 includes a curved transfer member 100 with an entrance aperture 104 for receiving crop material from the bottom of the elevator 40. The transfer auger 34 drives crop material into the bottom of the elevator 40 and into the bottom of the conveyor auger device 70. The transfer member 100, including the entrance aperture 104, defines a channel to a bottom chamber of the conveyor auger device 70. In FIG. 5, the conveyor auger device 70 includes an exit member 108 having a flat essentially rectangular face and an exit aperture 112 provided with or defining a channel for exiting of crop material from the upper conveyor housing portion 74 of the conveyor auger device 70 into the elevator 40.

Figure 6:
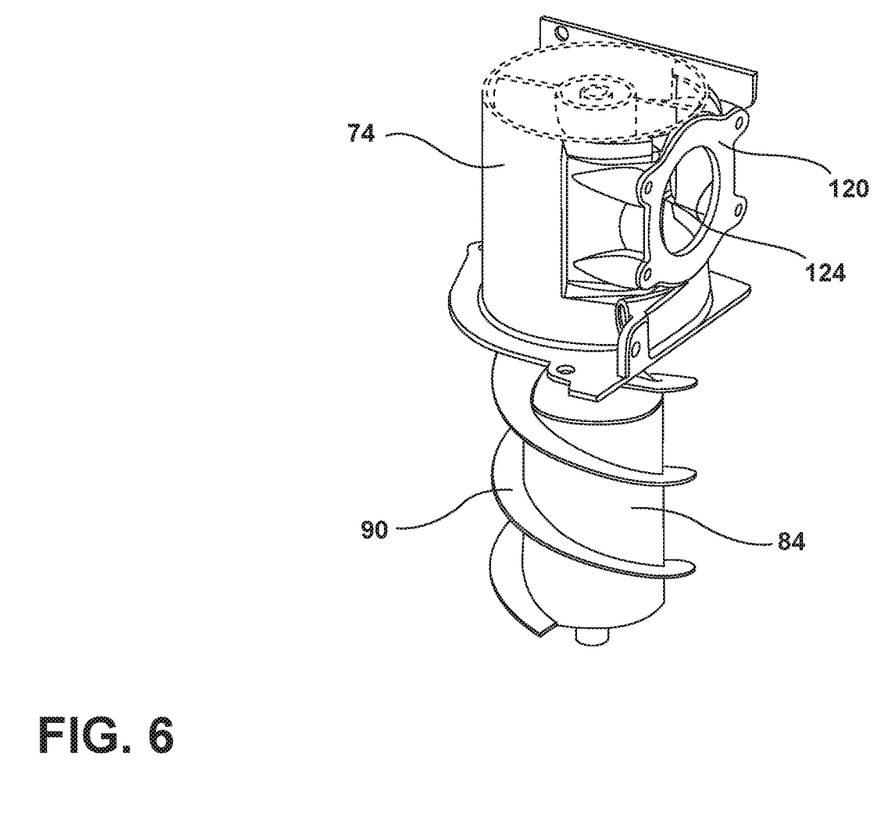
FIG. 6 is a partial perspective view of a conveyor auger device with a cut-away of a top portion thereof.

FIG. 6 is a partial cut-away view of the upper conveyor housing portion 74 showing a generally planar sensor receiving member 120 having a sensing aperture 124 that is in alignment with the section of the flight 90 that has a reduced radial extension orthogonal to the longitudinal axis L. The sensing aperture 124 is a laterally oriented sensing aperture in this embodiment. The sensor receiving member 120 has a planar shape disposed about the sensing aperture 124. The sensor receiving member 120 enables the sensor 64 to be located at or in the sensing aperture 124 of the conveyor auger device 70. The exit aperture 112 is disposed above the sensing aperture 124. Further, the exit aperture 112 is oriented in a different orthogonal direction than the sensing aperture 124. Thus, the flight 90 is spaced from the sensing aperture 124 a significant distance due to the reduced radial extension of the flight in section A. Accordingly, in the instance of the flight 90 being formed of a metal material, the metal material will not have an effect on the sensor 64 mounted onto the upper conveyor housing portion 74.

Figure 7:
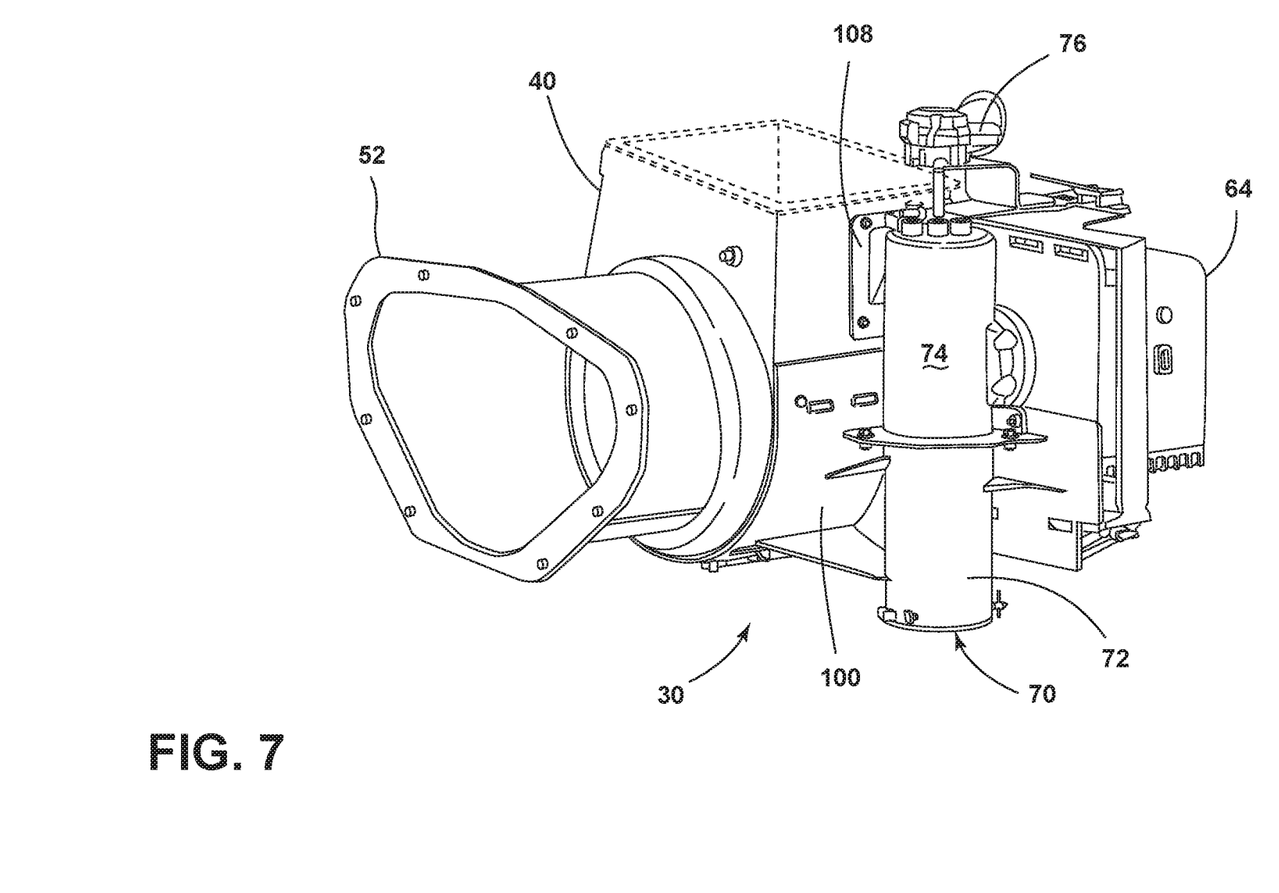
FIG. 7 is a close-up perspective partial view of a portion of the crop material transfer arrangement of FIG. 2 without the transfer auger or chain and paddle conveyor.

FIG. 7 shows how the sensor 64 is mounted to the conveyor auger device 70 essentially orthogonal to the curved transfer member 100 and the exit member 108 with respect to the longitudinal axis L. Thus, the entrance aperture 104 and the exit aperture 112 open in the same radial direction, while spaced apart a longitudinal linear distance. The sensing aperture 124, however, is located orthogonal respect to the longitudinal axis L and the entrance aperture 104 and the exit aperture 112 in the embodiment illustrated. Other arrangements are contemplated.

Operation

In operation, the transfer auger 34 provides crop material to the elevator 40 via the elevator receiver 52. While the chain and paddle conveyor 44 lift crop material to an upper storage tank, at the same time the sensing system 60 operates with the conveyor auger device 70 to provide crop material moving essentially continuously and upwardly past the sensor 64.

More specifically, the drum 84 of the conveyor auger 80 limits the amount of crop material entering the entrance aperture 104 thereof. As crop material enters the conveyor auger device 70, the flight 90 moves the crop material upwardly in a substantially vertical direction. When the crop material reaches section A, wherein the flight 90 is reduced in radial extension adjacent the sensing aperture 124 and the sensor 64, the crop material accumulates, while moving essentially continuously upwardly in the direction of the longitudinal axis L. Thus, the sensor 64 senses the presence of essentially continuously upwardly moving crop material adjacent the sensing aperture 124. Therefore, a greater amount of crop material is provided adjacent the sensor 64 than at lower portions of the flight 90. The increased amount of crop material adjacent the sensor 64 assists in proper sensing of the crop material or constituents thereof. Upon essentially continuous upward traveling of the crop material, the reverse flight 98 at a top end of the conveyor auger 80 ejects the crop material radially outward from the conveyor auger housing through the radially oriented exit aperture 112. The crop material either falls to a bottom of the elevator 40, or lands on a paddle 46 provided in the elevator. Thus, the conveyor auger 80 conveys crop material from a location in the harvester 10 upwardly beyond the sensor 64 disposed at the sensing aperture 124 for exiting the conveyor auger housing at the exit aperture 112 which opens radially into the elevator 40.

The sensor 64 disposed at the sensing aperture 124 obtains sensed information. From the sensed information, the arrangement determines a property of the crop material.

The conveyor auger device 70 thus acts as a bypass conveyor for sensing purposes. The crop material is returned to the elevator 40 for transfer to a storage tank at a top or upper part of the harvester 10.

Alternative Arrangements

While FIG. 2 shows the conveyor auger housing having a lower conveyor housing portion 72 and an upper conveyor housing portion 74, in another embodiment, a monolithic housing is provided.

In one embodiment, the sensor 64 is an imaging camera having a camera lens. One embodiment includes the camera lens as a flat planar lens and the imaging camera for sensing moisture for the crop material, and the crop material is a clean grain.

In one embodiment, the flight 90 is reduced in size/width adjacent the imaging camera of the sensor 64 in a region or area A so that a closest edge of the flight 90 is at least 15 millimeters from a camera lens of an imaging camera and/or from the sensing aperture 124. Thus, the flight 90 does not interfere with the sensor 64.

In one embodiment, the sensor 64 is a near infrared imaging camera having a camera lens disposed at/in the sensing aperture 124 for imaging the crop material to sense a property thereof. In one embodiment, the sensed property is moisture for the constituent of the crop material determined by images from the near infrared imaging camera. Determining other properties is contemplated. In one embodiment, a temperature sensor is provided as the sensor and in another embodiment, a combination of an imaging camera and an additional temperature sensor is contemplated In one embodiment, the crop material is ejected sidewardly with the reverse flight 98 disposed at an upper part of the conveyor auger 80 so that the crop material returns to a bottom of the elevator 40 that connects a bottom of the conveyor auger device 70. The embodiment includes moving the crop material from the bottom of the elevator 40 to a storage tank disposed at a top of the harvester 10 with the chain and paddle conveyor 44.

While the phrase "the crop material essentially continuously moving upwardly" is provided, the phrase does not preclude including some rotational movement about the longitudinal axis L of the conveyor auger 80 during upward movement thereof.

Thus, the disclosure provides, among other things, a sensing system for sensing a property of a crop material, including a conveyor auger having a reduced size or diameter for a flight adjacent a sensor. Various features and advantages of the disclosure are set forth in the following claims.

What is claimed is:

1. A sensing system for sensing a property of a crop material harvested by a harvester, the sensing system comprising:
   a conveyor auger device oriented in a substantially vertical direction, the conveyor auger device including a radially oriented sensing aperture, and a radially oriented exit aperture disposed upwardly above the sensing aperture;
   a conveyor auger disposed in the conveyor auger device, the conveyor auger including a flight for moving the crop material upwardly, wherein the flight has a reduced radial extension adjacent the sensing aperture; and
   a sensor disposed at or adjacent the sensing aperture for sensing the crop material that is moving essentially continuously upwardly for determining a property thereof.

2. The sensing system according to claim 1, wherein the conveyor auger device moves crop material from a location in the harvester upwardly beyond the sensor disposed at the sensing aperture for radially exiting the conveyor auger device at the exit aperture.

3. The sensing system according to claim 1, wherein the flight has an increased radial extension along a longitudinal axis of the conveyor auger above and below the sensing aperture.

4. The sensing system according to claim 1, wherein the sensor is an imaging camera having a camera lens.

5. The sensing system according to claim 4, wherein the camera lens is a flat planar lens and the imaging camera senses moisture for the crop material, and wherein the crop material is a clean grain.

6. The sensing system according to claim 1, wherein the sensor is a near infrared imaging camera having a camera lens disposed at or in the sensing aperture for imaging the crop material to sense a property thereof.

7. The sensing system according to claim 1, wherein the conveyor auger device includes a sensor receiving member having a planar shape disposed about the sensing aperture.

8. The sensing system according to claim 1, wherein the conveyor auger device includes a drum at a lower end thereof to reduce an amount of the crop material entering a bottom of the conveyor auger device.

9. A crop material transfer arrangement including a sensing system for sensing a property of a crop material harvested by a harvester, the crop material transfer arrangement comprising:
   a transfer auger configured to advance crop material;
   an elevator configured to receive crop material from the transfer auger, the elevator including a drive arrangement for moving the crop material to a storage tank of the harvester;
   a conveyor auger device oriented in a substantially vertical direction, the conveyor auger device configured to receive crop material from a bottom of the elevator and configured to return crop material to the elevator, the conveyor auger device including:
      a radially oriented sensing aperture,
      a radially oriented exit aperture disposed upwardly above the sensing aperture, and
      a conveyor auger including a flight for moving the crop material upwardly, wherein the flight has a reduced radial extension adjacent the sensing aperture; and
   a sensor disposed at or adjacent the sensing aperture for sensing the crop material that is moving essentially continuously upwardly for determining a property thereof.

10. The crop material transfer arrangement according to claim 9, wherein the sensor is an imaging camera for sensing moisture for the crop material, and wherein the crop material is a clean grain.

11. The crop material transfer arrangement according to claim 9, wherein the flight has an increased radial extension along a longitudinal axis of the conveyor auger above and below the sensing aperture.

12. The crop material transfer arrangement according to claim 9, wherein the drive arrangement of the elevator includes a chain and paddle conveyor configured for moving crop material from the bottom of the elevator to a storage tank disposed at a top of the harvester.

13. The crop material transfer arrangement according to claim 9, wherein the conveyor auger has a reverse flight at a top end thereof to eject crop material.

14. A method for sensing a property of a crop material harvested by a harvester, the method comprising:
   operating a conveyor auger to move the crop material generally upwardly within a conveyor auger device, the conveyor auger device having a sensing aperture;
   sensing essentially continuously upwardly moving crop material with a sensor disposed at the sensing aperture; and
   from the sensed information, determining a property of the crop material.

15. The method according to claim 14, wherein the conveyor auger has a reverse flight at a top thereof to eject crop material.

16. The method according to claim 14, wherein the sensor is an imaging camera, wherein the property of the crop material is moisture, and wherein the conveyor auger includes a flight having a reduced radial extension adjacent the sensing aperture.

17. The method according to claim 16, wherein the imaging camera is a near field imaging camera.

18. The method according to claim 14, wherein the imaging camera is a near infrared imaging camera that senses moisture for the crop material, and wherein the crop material is a clean grain.

19. The method according to claim 18, including moving the crop material from the bottom of the elevator to a storage tank disposed at a top of the harvester with a chain and paddle conveyor.

* * * * *